United States Patent
Zhu et al.

(10) Patent No.: US 9,650,402 B2
(45) Date of Patent: May 16, 2017

(54) HETERODINUCLEAR PLATINUM-RUTHENIUM COMPLEXES, PREPARATION THEREOF AND THERAPEUTIC USE THEREOF

(71) Applicant: City University of Hong Kong, Kowloon (HK)

(72) Inventors: Guangyu Zhu, Mid-Level West (HK); Lili Ma, Kowloon Tong (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 0 days.

(21) Appl. No.: 14/829,934

(22) Filed: Aug. 19, 2015

(65) Prior Publication Data

US 2017/0050997 A1 Feb. 23, 2017

(51) Int. Cl.
*A61K 31/555* (2006.01)
*C07F 15/00* (2006.01)

(52) U.S. Cl.
CPC ................ *C07F 15/0086* (2013.01)

(58) Field of Classification Search
USPC ............................................. 514/188; 546/2
See application file for complete search history.

(56) References Cited

PUBLICATIONS

Antonova, N.S. et al.: Theoretical characterization of a Ru N-heterocyclic carbene derivative of a polyoxometalate. Dalton Transac., vol. 40, pp. 2975-2982, 2011.*
Ma, et al, "Heterodinuclear Pt(IV)—Ru(II) anticancer prodrugs to combat both drug resistance and tumor metastasis," The Royal Society of Chemistry, Chem. Commun., 2016, 4 pages, 52, 10735.

* cited by examiner

*Primary Examiner* — Charanjit Aulakh
(74) *Attorney, Agent, or Firm* — Amin, Turocy & Watson, LLP

(57) ABSTRACT

A novel class of heterodinuclear Pt—Ru complexes are provided, and the methods for preparing the complexes are described. The inhibitory activities of the heterodinuclear Pt—Ru complexes against cancer/tumor cell growth, including cancer/tumor cells having a resistance to cisplatin, are further demonstrated.

26 Claims, 12 Drawing Sheets

Synthesis route of Pt(IV)(OH)(3-PyPA)

Crystal structure of Pt(IV)(OH)(3-PyPA)

Structures of [(ArRu)Ru(II)Cl($\mu$-Cl)$_2$Cl]$_2$

Synthesis route of Ruthplatin-1, 2 and 3

Synthesis route of Ruthplatin-4

Crystal structure of Ctrl-1

| Cell lines | cDDP | ruthplatin-1 (FI[a]) | ruthplatin-2 (FI[a]) | ruthplatin-3 (FI[a]) | ruthplatin-4 (FI[a]) | Pt(IV)(OH)(3-PyPA) |
|---|---|---|---|---|---|---|
| A2780 | 0.92 ± 0.30 | 0.12 ± 0.02 (7.7) | 0.12 ± 0.03 (7.7) | 0.12 ± 0.02 (7.7) | 0.09 ± 0.03 (10.2) | 1.38 ± 0.54 (1%DMF) (0.7) |
| A2780cisR | 16.01 ± 4.55 | 0.43 ± 0.01 (37.2) | 0.15 ± 0.09 (106.7) | 0.32 ± 0.06 (50.0) | 0.19 ± 0.03 (84.3) | 0.75 ± 0.08 (1%DMF) (21.3) |
| RF[b] | 17.4 | 3.6 | 1.3 | 2.7 | 2.1 | 0.5 |
| A549 | 4.31 ± 0.48 | 1.02 ± 0.21 (4.2) | 1.32 ± 0.09 (3.3) | 1.48 ± 0.14 (2.9) | 0.60 ± 0.09 (7.2) | ND |
| A549cisR | 24.01 ± 3.24 | 1.38 ± 0.01 (17.4) | 1.58 ± 0.46 (15.2) | 2.94 ± 0.55 (8.2) | 1.02 ± 0.29 (23.5) | ND |
| RF[b] | 5.6 | 1.4 | 1.2 | 2.0 | 1.7 | --- |
| HeLa | 3.35 ± 0.10 | 0.74 ± 0.11 (4.5) | 0.91 ± 0.16 (3.7) | 0.92 ± 0.04 (3.6) | 0.35 ± 0.04 (9.6) | ND |
| MDA-MB-231 | 9.15 ± 2.43 | 0.55 ± 0.23 (16.6) | ND | ND | ND | ND |
| MRC-5 | 1.02 ± 0.27 | 1.71 ± 0.67 (0.6) | 4.17 ± 1.14 (0.2) | 1.48 ± 0.74 (0.7) | 3.06 ± 1.53 (0.3) | 4.63 ± 1.36 (1% DMF) (0.2) |

TABLE 1. Cytotoxicity of Ruthplatin-1, 2, 3 and 4

FIG. 9

| Cell lines | IC$_{50}$ ± SD (µM) (72 h MTT) | | | |
| --- | --- | --- | --- | --- |
| | cDDP | Ctrl-1 | cDDP+Ctrl-1 (FI[a]) | ruthplatin-1 (FI[a]) |
| A2780 | 0.92 ± 0.30 | >30 | 0.74 ± 0.43 (1.2) | 0.12 ± 0.02 (7.7) |
| A2780cisR | 16.01 ± 4.55 | >30 | 14.20 ± 0.86 (1.1) | 0.43 ± 0.01 (37.2) |
| RF[b] | 17.4 | NA | NA | 3.6 |
| A549 | 4.31 ± 0.48 | >80 | 5.26 ± 0.38 (0.8) | 1.02 ± 0.21 (4.2) |
| A549cisR | 24.01 ± 3.24 | >80 | 23.86 ± 1.94 (1.0) | 1.38 ± 0.01 (17.4) |
| RF[b] | 5.6 | NA | NA | 1.4 |
| MDA-MB-231 | 9.15 ± 2.43 | >200 | 11.25 ± 9.43 (0.8) | 0.55 ± 0.23 (16.6) |

TABLE 2. Cytotoxicity of Ruthplatin-1 and Ctrl-1

FIG. 10

HETERODINUCLEAR PLATINUM-RUTHENIUM COMPLEXES, PREPARATION THEREOF AND THERAPEUTIC USE THEREOF

TECHNICAL FIELD

This application generally relates to heterodinuclear platinum-ruthenium (Pt—Ru) complexes, preparation thereof, and therapeutic use thereof in treatment of disease, especially cancer.

BACKGROUND

Platinum-based anticancer drugs, such as cisplatin, have been extensively used to treat different types of cancer patients. Cisplatin (also referred to as cDDP) is a chemotherapy drug and was the first member of a class of platinum containing anti-cancer drugs, which now also includes carboplatin and oxaliplatin. These platinum complexes react in vivo, binding to and causing crosslinking of DNA, which ultimately triggers apoptosis.

Although more than 50% of cancer patients have been treated with platinum-based anticancer drugs, these drugs produce highly toxic side effects. In addition, many patients treated with these platinum-based anticancer drugs develop drug resistance thereto. Therefore, it is desirable to develop new anticancer agents that can be used as alternatives to the clinical chemotherapeutic drugs, such as cDDP, especially for patients after the development of chemoresistance using current drugs.

BRIEF DESCRIPTION OF THE DRAWINGS

Numerous aspects, embodiments, objects and advantages of the present invention will be apparent upon consideration of the following detailed description, taken in conjunction with the accompanying drawings, in which like reference characters refer to like parts throughout, and in which:

FIG. 9 presents Table 1 depicting the resulting cytotoxicity of ruthplatin-1, 2 and 3 as compared to the resulting cytotoxicity of cDDP in accordance with various aspects and embodiments described herein;

FIG. 10 presents Table 2 depicting the resulting cytotoxicity of ruthplatin-1, Ctrl-1 and cDDP combined with Ctrl-1, as compared to the resulting cytotoxicity of cDDP, in accordance with various aspects and embodiments described herein;

DETAILED DESCRIPTION

Figure 1:
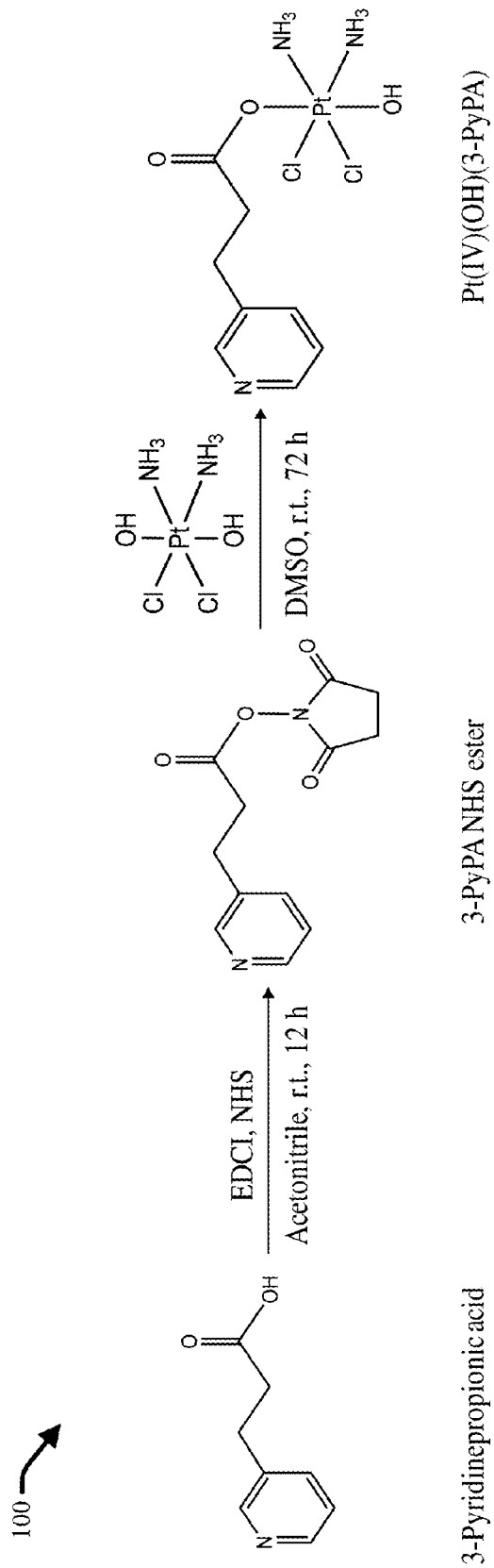
FIG. 1 presents the synthesis route of Pt(IV)(OH)(3-PyPA) in accordance with various aspects and embodiments described herein.

The innovation is described with reference to the drawings, wherein like reference numerals are used to refer to like elements throughout. In the following description, for purposes of explanation, numerous specific details are set forth in order to provide a thorough understanding of this innovation. It may be evident, however, that the innovation can be practiced without these specific details. In other instances, well-known structures and components are shown in block diagram form in order to facilitate describing the innovation.

By way of introduction, the subject matter described in this disclosure provides a novel class of heterodinuclear Pt—Ru complexes for the treatment of diseases especially cancer, including the preparation of the compounds and their inhibitory activities against cancer/tumor cell growth. The subject disclosure also relates to a pharmaceutical composition including at least one heterodinuclear Pt—Ru complex and a suitable drug carrier. The subject heterodinuclear Pt—Ru complexes have been shown to demonstrate significant activity against cancer and/or tumor cell growth. Further, the subject heterodinuclear Pt—Ru complexes are very effective in killing cDDP-resistant cells. Thus one advantage associated with usage of the subject heterodinuclear Pt—Ru complexes as an anti-cancer drug is the effectiveness of the subject heterodinuclear Pt—Ru complexes in killing cancer or tumor cells that exhibit a resistance to cDDP. Moreover, the subject heterodinuclear Pt—Ru complexes exhibit a lower toxicity to non-cancerous cells relative to existing platinum-based anticancer drugs, such as cDDP.

In an aspect, the subject heterodinuclear Pt—Ru complexes can be used as a single agent for treating subjects with cancer. The term 'subject' used in this context herein refer to a living organism and can include but is not limited, human, plant and animal subjects. In another aspect, the subject heterodinuclear Pt—Ru complexes can be used in a combination therapy regimen together with other types of anti-cancer drugs. Some examples of heterodinuclear Pt—Ru complexes are shown below, though claimed subject matter is not so limited.

In one or more embodiments, a heterodinuclear Pt—Ru complex includes the molecular structure of Structure I:

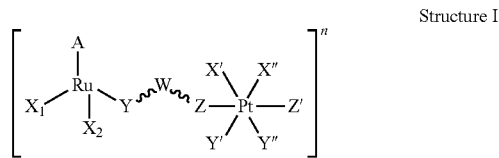

Structure I wherein $X_1$, $X_2$, X', X", Y, Y', Y", Z, Z' are selected from electron donor ligands, including but not limited to nitrogen (N)-containing ligands, oxygen (O)-containing ligands, phosphorous (P)-containing ligands, sulfur (S)-containing ligands, and halogen containing ligands, wherein A is an arene, and wherein W is a linker unit with any length to link Y and Z together. All the metal-coordinating ligands are either independent or linked. In some aspects, n is neutral, represented by n=0. In other aspects, n is any positive charge or any negative charge. A heterodinuclear Pt—Ru complex having the molecular structure of Structure I is effective in the treatment of disease, particularly cancer.

In accordance with these embodiments, a heterodinuclear Pt—Ru having the molecular structure of Structure I can further embody Structures II-V below.

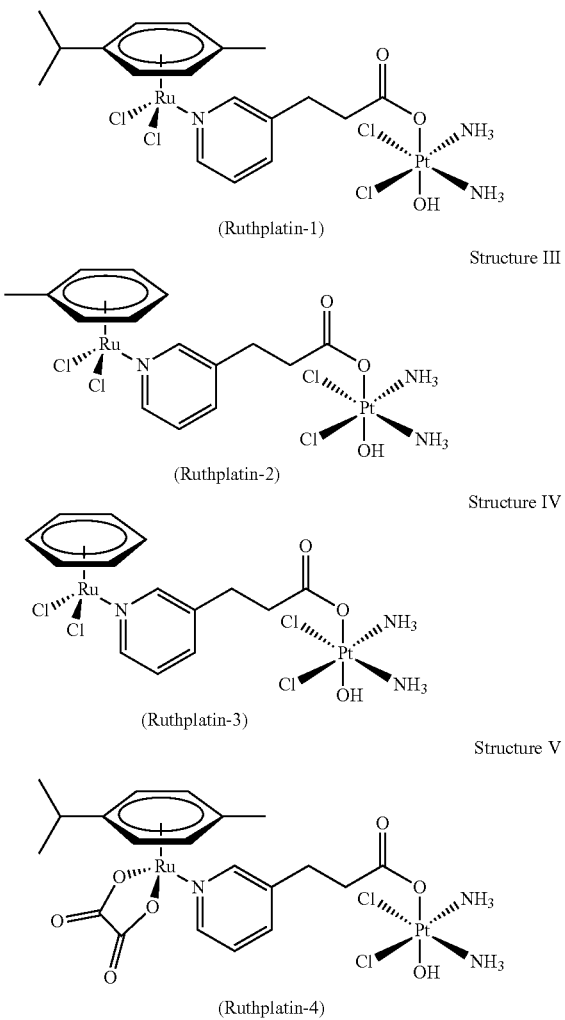

(Ruthplatin-1)

Structure II (Ruthplatin-2)

Structure III (Ruthplatin-3)

Structure IV (Ruthplatin-4)

Structure V

In other embodiments, a heterodinuclear Pt—Ru complex includes the molecular structure of Structure VI:

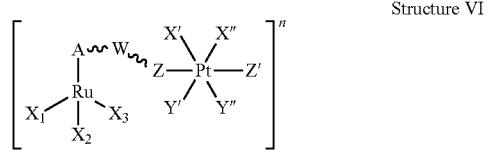

Structure VI wherein $X_1$, $X_2$, $X_3$, X', X", Y', Y", Z, Z' are selected from electron donor ligands including but not limited to N-containing ligands, O-containing ligands, P-containing ligands, S-containing ligands, halogens, and other suitable ligands, wherein A is an arene, and wherein W is a linker unit with any length to link A and Z together. All the metal-coordinating ligands are either independent or linked. In some aspects, n is neutral, represented by n=0. In other aspects, n is any positive charge or any negative charge. A heterodinuclear Pt—Ru complex having the molecular structure of Structure VI is also effective in the treatment of disease, particularly cancer.

In other embodiments, a heterodinuclear Pt—Ru complex includes the molecular structure of Structure VII:

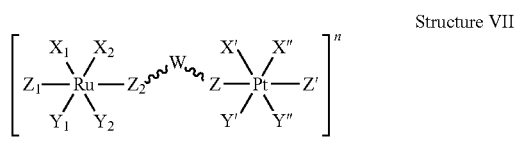

Structure VII wherein $X_1$, $X_2$, X', X", $Y_1$, $Y_2$, Y', Y", $Z_1$, $Z_2$, Z, Z' are selected from electron donor ligands including but not limited to N-containing ligands, O-containing ligands, P-containing ligands, S-containing ligands, halogens, and other suitable ligands, and herein W is a linker unit with any length to link $Z_2$ and Z together. All the metal-coordinating ligands are either independent or linked. In some aspects, n is neutral, represented by n=0. In other aspects, n is any positive charge or any negative charge. A heterodinuclear Pt—Ru complex having the molecular structure of Structure VII is effective in the treatment of disease, particularly cancer.

In other embodiments, a heterodinuclear Pt—Ru complex includes the molecular structure of Structure VIII:

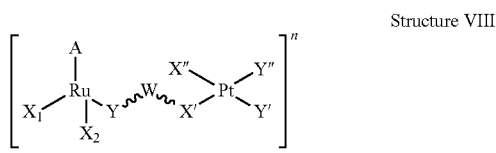

Structure VIII wherein $X_1$, $X_2$, X', X", Y, Y', Y" are selected from electron donor ligands including but not limited to N-containing ligands, O-containing ligands, P-containing ligands, S-containing ligands, halogens, and other suitable ligands, wherein A is an arene, and wherein W is a linker unit with any length to link Y and X' together. All the metal-coordinating ligands are either independent or linked. In some aspects, n is neutral, represented by n=0. In other aspects, n is any positive charge or any negative charge. A heterodinuclear Pt—Ru complex having the molecular structure of Structure VIII is also effective in the treatment of disease, particularly cancer.

In other embodiments, a heterodinuclear Pt—Ru complex includes the molecular structure of Structure IX:

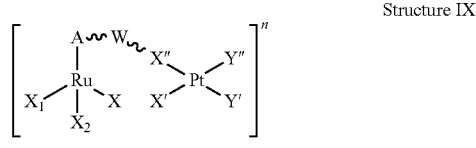

Structure IX wherein X, X₁, X₂, X', X", Y', Y" are selected from electron donor ligands including but not limited to N-containing ligands, O-containing ligands, P-containing ligands, S-containing ligands, halogens, and other suitable ligands, wherein A is an arene, and wherein W is a linker unit with any length to link A and X" together. All the metal-coordinating ligands are either independent or linked. In some aspects, n is neutral, represented by 0. In other aspects, n is any positive charge or any negative charge. A heterodinuclear Pt—Ru complex having the molecular structure of Structure IX is also effective in the treatment of disease, particularly cancer.

In other embodiments, a heterodinuclear Pt—Ru complex includes the molecular structure of Structure X:

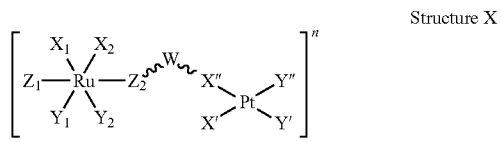

Structure X wherein $X_1$, $X_2$, X', X", $Y_1$, $Y_2$, Y', Y", $Z_1$, $Z_2$ are selected from electron donor ligands including but not limited to N-containing ligands, O-containing ligands, P-containing ligands, S-containing ligands, halogens, and other suitable ligands, and wherein W is a linker unit with any length to link $Z_2$ and X" together. All the metal-coordinating ligands are either independent or linked. In some aspects, n is neutral, represented by n=0. In other aspects, n is any positive charge or any negative charge. A heterodinuclear Pt—Ru complex having the molecular structure of Structure X is also effective in the treatment of disease, particularly cancer. In various additional embodiments, methods for treating cancer or tumor of a subject are provided that include administering, to the subject, an effective amount of a pharmaceutical composition including a heterodinuclear Pt—Ru complex as the active agent with a chemical/molecular structure of Structures I-IX. In an aspect, the pharmaceutical composition includes an effective amount of the heterodinuclear Pt—Ru complex as the active agent and a suitable drug carrier.

In an aspect, the pharmaceutical composition is administered orally. In another aspect, the pharmaceutical composition is administered intravenously. Still in yet another aspect, the pharmaceutical composition is administered in combination with one or more other anti-cancer therapies, including but not limited to: chemotherapy, radiation therapy, hormonal therapy, and targeted therapy (including immunotherapy such as monoclonal antibody therapy).

Based on administration of the pharmaceutical composition to a subject having cancer or a tumor, the growth of cancer cells or tumor cells of the subject is inhibited. In some aspects, existing cancer cells or tumor cells of the subject undergo apoptosis as a result of administering of the pharmaceutical composition. In an aspect, prior to administration of the pharmaceutical composition, the cancer or the tumor cells of the subject have demonstrated a resistance to cDDP. However, despite the resistance of the cancer or the tumor cells to cDDP, the cancer or the tumor cells are undergo apoptosis and/or growth of additional cancer or tumor cells is inhibited.

1—Synthesis and Characterizations

In various embodiments, the subject heterodinuclear Pt—Ru complexes such as those shown above (e.g., the heterodinuclear Pt—Ru complexes having structures I-VII) can be prepared by reacting Pt(IV)(OH)(3-PyPA) with [(arene)Ru(II)Cl(μ-Cl)₂]₂. The resulting heterodinuclear Pt—Ru complexes are referred to by the chemical composition name of ruthplatin. All reactions described herein were carried out under protection of Argon unless otherwise noted. Agents and solvents were used as received without further drying or purification.

Platinum and ruthenium contents were determined by an inductively coupled plasma-optical emission spectrometer (ICP-OES, Optima 2100DV, PerkinElmer, USA). Elemental analysis was tested by using a vario micro elemental analyzer. ¹H, ¹³C, and ¹⁹⁵Pt NMR spectra were measured by a Bruker Ultrashield™ 300, 400, or 600 MHz NMR spectrometer at room temperature. All NMR chemical shifts (δ) are reported in parts per million (ppm) and referenced as described below. ¹H and ¹³C NMR spectra were referenced internally to residual solvent peaks using deuterated dimethyl sulfoxide (DMSO-d₆), deuterated dimethyl formamide (DMF-d₇) or deuterated chloroform (CDCl₃) as the solvents. ¹⁹⁵Pt NMR spectrum was referenced by using external standards of K₂PtCl₄ in D₂O (δ=−1628 ppm).

1.1—Synthesis of Pt(IV)(OH)(3-PyPA)

FIG. 1 presents the synthesis route 100 of Pt(IV)(OH)(3-PyPA) in accordance with various aspects and embodiments described herein.

Synthesis of 3-PyPA NHS ester 50 mL acetonitrile (A.R.) was added to a mixture of 3-Pyridinepropionic acid (1.0 g, 6.62 mmol), NHS (N-Hydroxysuccinimide, 0.914 g, 7.28 mmol) and EDCI (1-Ethyl-3-(3-dimethylaminopropyl) carbodiimide, 1.52 g, 7.28 mmol) to get a suspension. After stirring at room temperature (r.t.) for 12 hours (h), a colorless solution was obtained. Acetonitrile was removed by rotary evaporation to give out a white-yellow raw product. It was dissolved in DCM (dichloromethane), and washed with water. DCM phase was collected and a white powder was gained by removing the solvent. Yield: 1.0 g, 61%. ¹H NMR (300 MHz, DMSO-d₆) $\delta_{ppm}$ 8.53 (d, J=2.0 Hz, 1H, py), 8.43 (dd, J=4.7, 1.3 Hz, 1H, py), 7.74 (d, J=7.8 Hz, 1H, py), 7.33 (dd, J=7.8, 4.8 Hz, 1H, py), 3.08 (t, J=7.2 Hz, 2H, CH₂), 2.96 (dd, J=18.5, 11.0 Hz, 2H, CH₂), 2.81 (s, 4H, 2CH₂).

Synthesis of Pt(IV)(OH)(3-PyPA)

A solution of 3-PyPA NHS ester (446.5 mg, 1.80 mmol) in DMSO (dimethyl sulfoxide, extra dry, 20 mL), was added dropwise to a suspension of oxoPt(IV) (400 mg, 1.20 mmol) in DMSO (extra dry, 30 mL) with vigorously stirring. The mixture was stirring at r.t. for 72 h, then a lot of Et₂O was added to the yellow solution to get white precipitate. The light-yellow precipitate was washed with DCM and dried. White powder. Yield: 400.0 mg, 71.4%. ¹H NMR (400 MHz, DMF-d₇) $\delta_{ppm}$ 8.49 (d, J=1.9 Hz, 1H), 8.41 (dd, J=4.7, 1.5 Hz, 1H), 7.71 (d, J=7.8 Hz, 1H), 7.29 (dd, J=7.8, 4.8 Hz, 1H), 6.57-6.07 (m, 7H), 2.84 (t, J=7.7 Hz, 2H), 2.52 (t, J=7.7 Hz, 2H), 1.28 (s, 1H). ¹³C NMR (100 MHz, DMF-d₇) $\delta_{ppm}$ 181.58, 150.95, 148.30, 138.51, 136.93, 124.41, 41.53, 38.78. ¹⁹⁵Pt NMR (129 MHz, DMSO-d₆) $\delta_{ppm}$ 1050.80. The crystal for X-ray diffraction was obtained by diffusing a mixture of DCM/Et₂O to the solution of Pt(IV)(OH)(3-PyPA) in DMSO.

Figure 2:
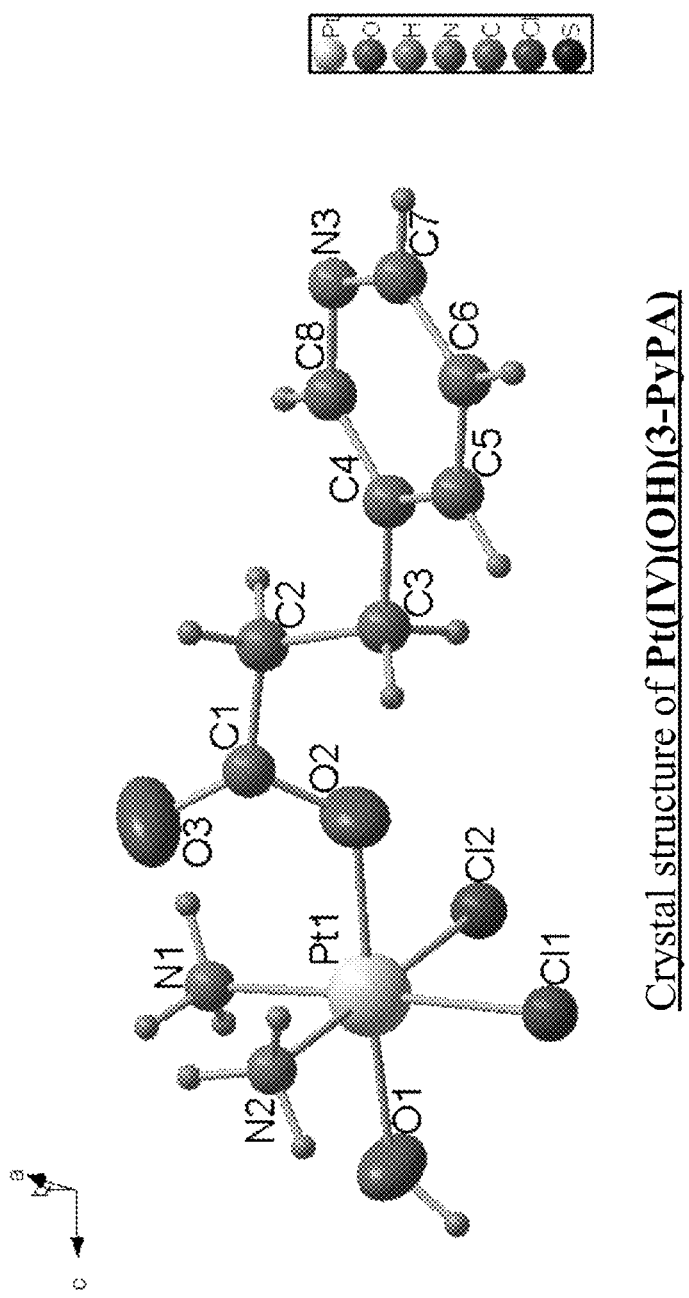
FIG. 2 presents the crystal structure of Pt(IV)(OH)(3-PyPA) in accordance with various aspects and embodiments described herein.

FIG. 2 presents the crystal structure of Pt(IV)(OH)(3-PyPA).

1.2—Synthesis of [(arene)Ru(II)Cl(μ-Cl)$_2$]$_2$

Figure 3:
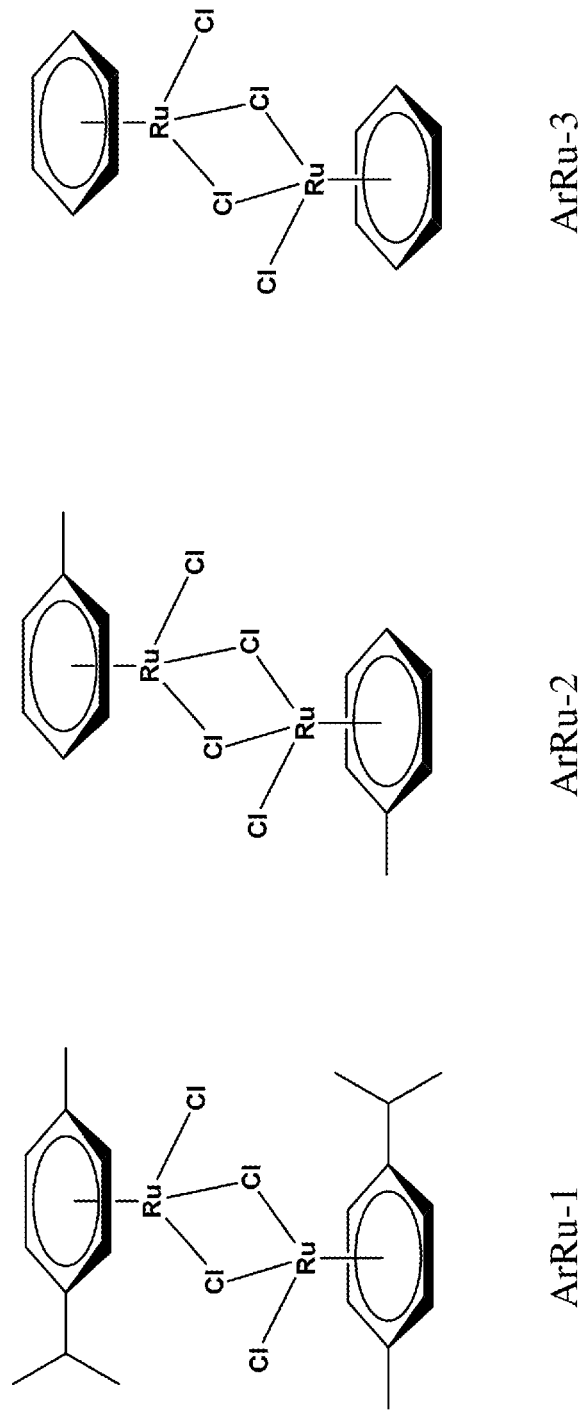
FIG. 3 presents the various structures of [(arene)Ru(II)Cl (µ-Cl)$_2$]$_2$ in accordance with various aspects and embodiments of the subject disclosure

FIG. 3 presents the various structures of [(arene)Ru(II)Cl(μ-Cl)$_2$]$_2$ in accordance with various aspects and embodiments of the subject disclosure. These structures include ArRu-1 [(η$^6$-p-cym)Ru(II)Cl(μ-Cl)$_2$]$_2$, ArRu-2 [(π-methyl-C$_6$H$_6$)Ru(II)Cl(μ-Cl)$_2$]$_2$, and ArRu-3 [(π-C$_6$H$_6$)Ru(II)Cl(μ-Cl)$_2$]$_2$. ArRu-1, 2 and 3 were synthesized according to previous reports, wherein hydrated RuCl$_3$ and excess amount of corresponding diene (α-phellandrene, 1-methyl-1,4-cyclohexadiene and 1,3-cyclohexadiene) was refluxed in ethanol for 12 hours. The red or brown-red precipitates were then filtrated and washed with ethanol and Et$_2$O. A red or brown-red powder was then obtained by drying. ArRu-1 [(η$^6$-p-cym)Ru(II)Cl(μ-Cl)$_2$]$_2$ includes $^1$H NMR (400 MHz, DMF-d$_7$) δ$_{ppm}$ 5.68 (d, J=5.9 Hz, 2H), 5.45 (d, J=5.9 Hz, 2H), 2.99-2.90 (m, 1H, CH), 2.19 (s, 3H, CH$_3$), 1.33 (d, J=6.9 Hz, 6H, 2CH$_3$). ArRu-2 [(π-methyl-C$_6$H$_6$)Ru(II)Cl(μ-Cl)$_2$]$_2$ includes $^1$H NMR (300 MHz, DMF-d$_7$) δ$_{ppm}$ 5.81 (t, J=5.7 Hz, 2H, arene), 5.60 (t, J=5.5 Hz, 1H, arene), 5.52 (d, J=5.8 Hz, 2H, arene), 2.20 (s, 3H, CH$_3$). $^{13}$C NMR (75 MHz, DMF-d$_7$) δ$_{ppm}$ 99.05, 85.91, 80.01, 76.81, 18.99. ArRu-3 [(π-C$_6$H$_6$)Ru(II)Cl(μ-Cl)$_2$]$_2$ includes $^1$H NMR (400 MHz, DMSO-d$_6$) δ$_{ppm}$ 5.98 (d, J=0.6 Hz, 6H).

1.3—Synthesis of Ruthplatin-1, 2 and 3

Figure 4:
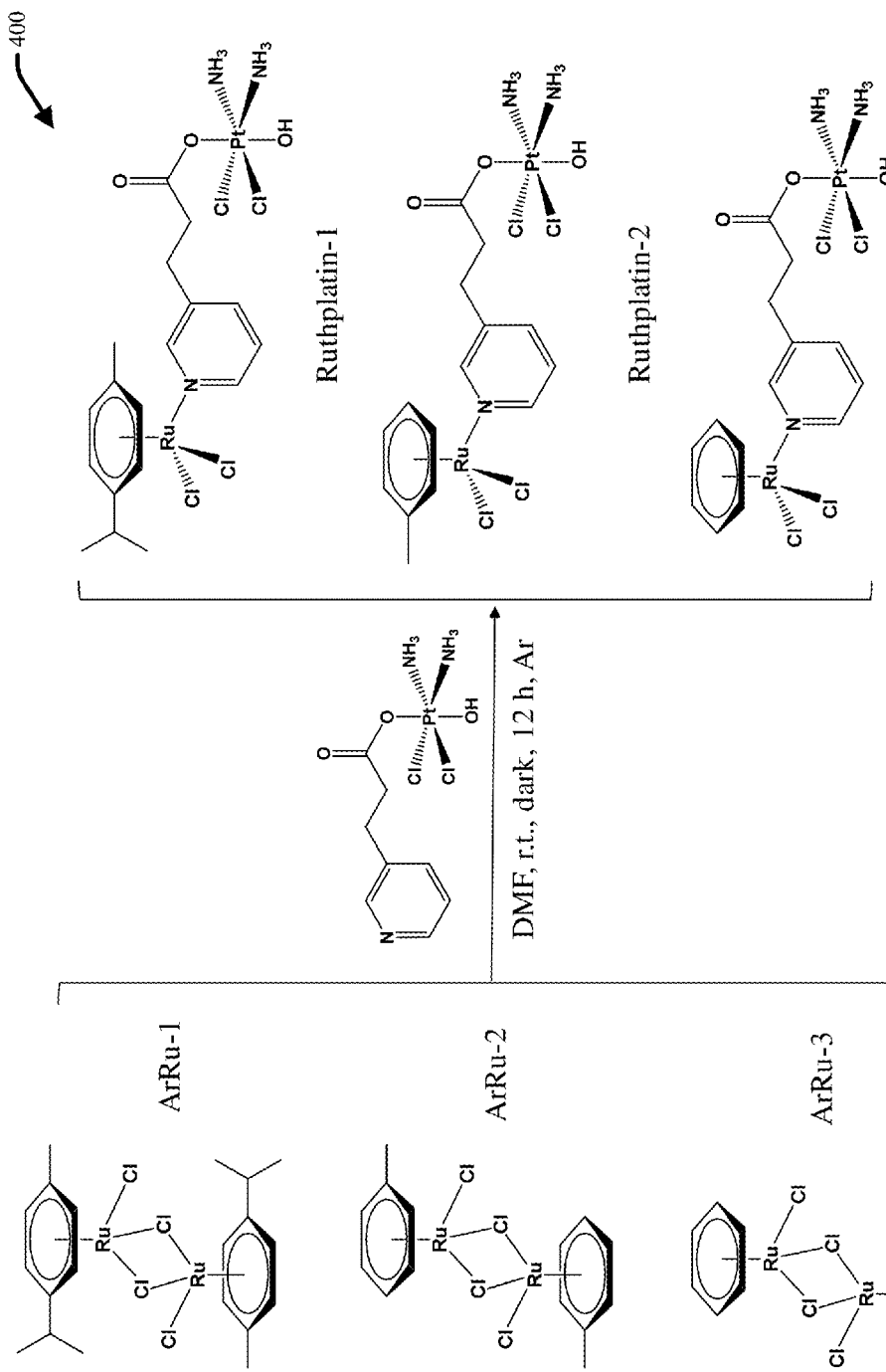
FIG. 4 presents the synthesis route of example heterodinuclear Pt—Ru complexes, referred to herein as Ruthplatin-1, 2 and 3, in accordance with various aspects and embodiments described herein.

FIG. 4 presents the synthesis route 400 of example heterodinuclear Pt—Ru complexes, referred to herein as Ruthplatin 1, 2 and 3, in accordance with various aspects and embodiments described herein.

Synthesis of Ruthplatin-1

[(η$^6$-p-cym)Ru(II)Cl(μ-Cl)$_2$]$_2$ (65.5 mg, 0.107 mmol) and Pt(IV)(OH)(3-PyPA) (100.0 mg, 0.214 mmol) were stirring in DMF (20 mL) at r.t. in dark for 12 h. Then Et$_2$O was added to the filtered solution to get a yellow precipitate. It was separated by centrifuge and washed by Et$_2$O to give a yellow powder. Yield: 110.0 mg, 66.5%. $^1$H NMR (400 MHz, DMF-d$_7$) δ$_{ppm}$ 8.91 (s, 1H, py), 8.85 (d, J=5.5 Hz, 1H, py), 7.88 (d, J=8.0 Hz, 1H, py), 7.39 (dd, J=7.6, 5.8 Hz, 1H, py), 6.34 (dd, J=64.6, 38.1 Hz, 6H, NH$_3$), 5.65 (d, J=6.0 Hz, 2H, arene), 5.47 (d, J=5.9 Hz, 2H, arene), 2.95-2.89 (m, 1H, CH), 2.86 (t, J=7.5 Hz, 2H, CH$_2$), 2.56 (t, J=7.5 Hz, 2H, CH$_2$), 2.01 (s, 3H, CH$_3$), 1.31 (d, J=6.9 Hz, 6H, 2CH$_3$). $^{13}$C NMR (100 MHz, DMF-d$_7$) δ$_{ppm}$ 180.40, 155.34, 152.59, 138.38, 138.23, 124.02, 102.25, 97.42, 83.72, 81.98, 37.42, 30.89, 21.94. $^{195}$Pt NMR (129 MHz, DMF-d$_7$) δ$_{ppm}$ 996.01. Calcd for C$_{18}$H$_{30}$Cl$_4$N$_3$O$_{3.5}$PtRu: C, 27.63; H, 3.86; N, 5.37. Found: C, 27.31; H, 3.99; N, 6.00.

Ruthplatin-2 was synthesized with the same method as Ruthplatin-1. Yellow powder. Yield: 100.0 mg, 57.5%. $^1$H NMR (400 MHz, DMF-d$_7$) δ$_{ppm}$ 8.95 (s, 1H, py), 8.87 (d, J=5.2 Hz, 1H, py), 7.87 (d, J=7.9 Hz, 1H, py), 7.36 (dd, J=7.6, 5.8 Hz, 1H, py), 6.60-6.08 (m, 6H, NH$_3$), 5.79 (t, J=5.6 Hz, 2H, arene), 5.71 (t, J=5.4 Hz, 1H, arene), 5.51 (d, J=5.7 Hz, 2H, arene), 2.84 (d, J=7.4 Hz, 2H, CH$_2$), 2.56 (d, J=7.4 Hz, 2H, CH$_2$), 2.11 (s, 3H, CH$_3$). $^{13}$C NMR (100 MHz, DMF-d$_7$) δ$_{ppm}$ 181.26, 156.46, 153.70, 139.18, 139.06, 124.76, 101.28, 88.52, 81.98, 80.40, 38.26, 36.50, 19.18. $^{195}$Pt NMR (129 MHz, DMF-d$_7$) δ$_{ppm}$ 988.55. Calcd for C$_{15}$H$_{23}$Cl$_4$N$_3$O$_3$PtRu: C, 24.4; H, 3.17; N, 5.75. Found: C, 24.66; H, 3.51; N, 6.04.

Ruthplatin-3 was synthesized with the same method as Ruthplatin-1 and 2. Brown powder. Yield: 105.0 mg, 55.6%. $^1$H NMR (400 MHz, DMF-d$_7$) δ$_{ppm}$ 8.98 (s, 1H, py), 8.89 (d, J=5.0 Hz, 1H, py), 7.87 (d, J=7.9 Hz, 1H, py), 7.36 (dd, J=7.8, 5.6 Hz, 1H, py), 6.55-6.03 (m, 6H, NH$_3$), 5.82 (s, 6H, arene), 2.85 (t, J=7.3 Hz, 2H, CH$_2$), 2.56 (t, J=7.3 Hz, 2H, CH$_2$). $^{13}$C NMR (100 MHz, DMF-d$_7$) δ$_{ppm}$ 180.23, 155.49, 152.67, 138.16, 138.10, 123.72, 84.53, 37.18, 35.50. Calcd for C$_{14}$H$_{21}$Cl$_4$N$_3$O$_3$PtRu: C, 23.44; H, 2.95; N, 5.86. Found: C, 22.76; H, 3.24; N, 6.56.

1.4—Synthesis of Ruthplatin-4

Figure 5:
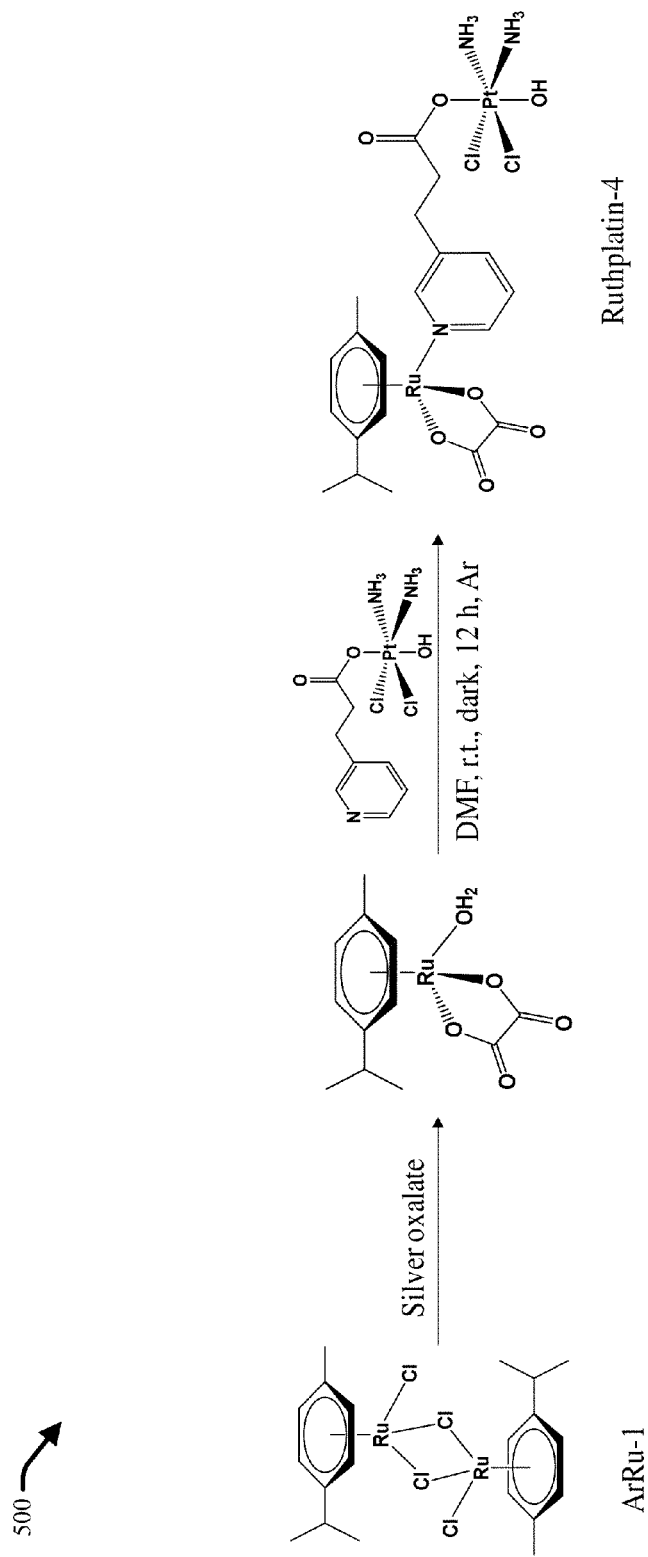
FIG. 5 presents the synthesis route of another example heterodinuclear Pt—Ru complexes, referred to herein as Ruthplatin-4, in accordance with various aspects and embodiments described herein.

FIG. 5 presents the synthesis route 500 of another example heterodinuclear Pt—Ru complex, referred to herein as Ruthplatin-4, in accordance with various aspects and embodiments described herein.

Synthesis of [(η$^6$-p-cym)Ru(II)(O^O)]

Silver oxalate (372.3 mg, 0.196 mmol) was added to a aqueous solution of [(η$^6$-p-cym)Ru(II)Cl(μ-Cl)$_2$]$_2$ (300.0 mg, 0.490 mmol), and stirred at r.t. for 2 h, shielding from light. The obtained orange solution was frozen to dry to give out an orange powder. Yield: 237.0 mg, 70.9%.

Synthesis of Ruthplatin-4

Ruthplatin-4 was synthesized by the reaction of [(η$^6$-p-cym)Ru(II)(O^O)] (40.0 mg, 0.117 mmol) and Pt(IV)(OH)(3-PyPA) (67.4 mg, 0.144 mmol) in DMF (10 mL) at r.t. in dark for 12 h. An orange solution was collected by filtration and Et$_2$O was added to get orange precipitate. Orange powder was gained by drying, after washing by Et$_2$O. Yield: 59.0 mg, 54.9%. $^1$H NMR (400 MHz, DMF-d$_7$) δ$_{ppm}$ 8.57 (s, 1H, py), 8.36 (d, J=5.4 Hz, 1H, py), 7.95 (d, J=7.9 Hz, 1H, py), 7.52 (dd, J=7.7, 5.6 Hz, 1H, py), 6.63-6.15 (m, 6H, NH$_3$), 5.96 (d, J=6.0 Hz, 2H, arene), 5.74 (d, J=6.0 Hz, 2H, arene), 2.99-2.85 (m, 3H, CH, CH$_2$), 2.61-2.52 (m, 2H, CH$_2$), 2.13 (s, 3H, CH$_3$), 1.33 (d, J=6.8 Hz, 6H, 2CH$_3$). $^{13}$C NMR (100 MHz, DMF-d$_7$) δ$_{ppm}$ 179.74, 164.96, 153.15, 150.43, 139.99, 139.41, 125.22, 101.16, 97.54, 83.09, 80.39, 37.08, 30.90, 21.93.

1.5—Synthesis of Ctrl-1, 2 and 3

Figure 6:
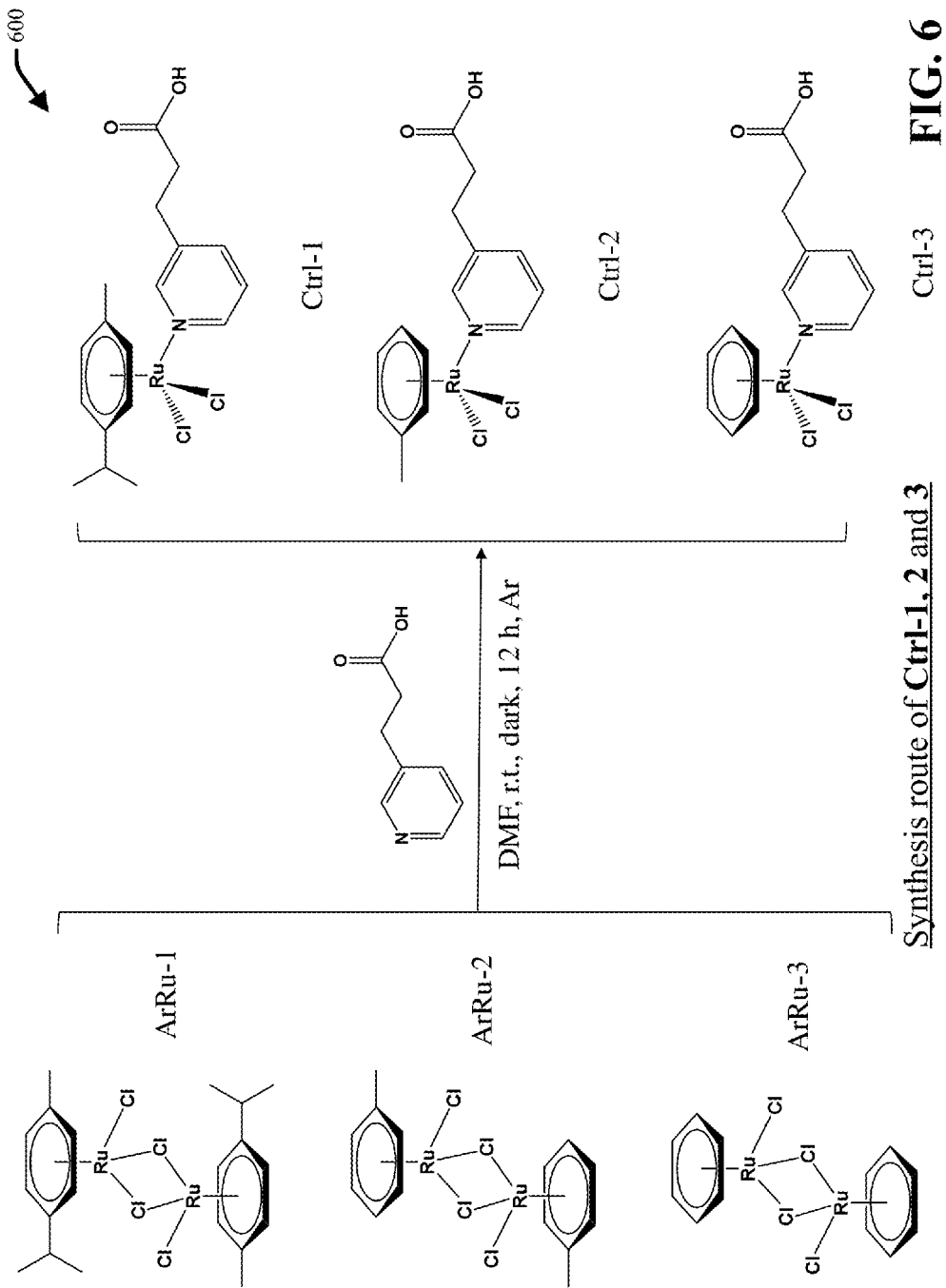
FIG. 6 presents the synthesis route of example control chemical complexes Ctrl-1, 2 and 3 in accordance with various aspects and embodiments described herein.

FIG. 6 presents the synthesis route 600 of example control chemical complexes Ctrl-1-3, against which the cytotoxicity of the subject heterodinuclear Pt—Ru complexes were tested. Complexes Ctrl 1-3 are ruthenium-based anticancer agents and serve as controls for comparison with the cytotoxicity from heterodinuclear Pt—Ru complexes. A comparison between the cytotoxicity of Ruthplatin-1 and the control chemical complex Ctrl-1, is presented below in section 2.2.

Synthesis of Ctrl-1

3-Pyridinepropionic acid (24.7 mg, 0.163 mmol) was added to a solution of [(η$^6$-p-cym)Ru(II)Cl(μ-Cl)$_2$]$_2$ (50.0 mg, 0.082 mmol) in DCM (10 mL) and it was stirred for 12 h at r.t. in dark. Then Et$_2$O was added to the filtered solution to get a yellow precipitate, the precipitated was filtered and washed by Et$_2$O to give a yellow powder. Yield: 65.0 mg, 86.7%. $^1$H NMR (400 MHz, CDCl$_3$) δ$_{ppm}$ 8.95 (s, 1H, py), 8.90 (d, J=5.7 Hz, 1H, py), 7.61 (d, J=7.8 Hz, 1H, py), 7.23 (s, 1H, py), 5.45 (d, J=5.9 Hz, 2H, arene), 5.22 (d, J=5.8 Hz, 2H, arene), 3.69-3.35 (m, 1H, COOH), 2.98 (t, J=7.0 Hz, 2H, $CH_2$), 2.71 (t, J=7.1 Hz, 2H, $CH_2$), 2.08 (s, 3H, $CH_3$), 1.31 (d, J=6.9 Hz, 6H, $2CH_3$). The crystal for X-ray diffraction was obtained by diffusing $Et_2O$ to the solution of Ctrl-1 in DMF.

Figure 7:
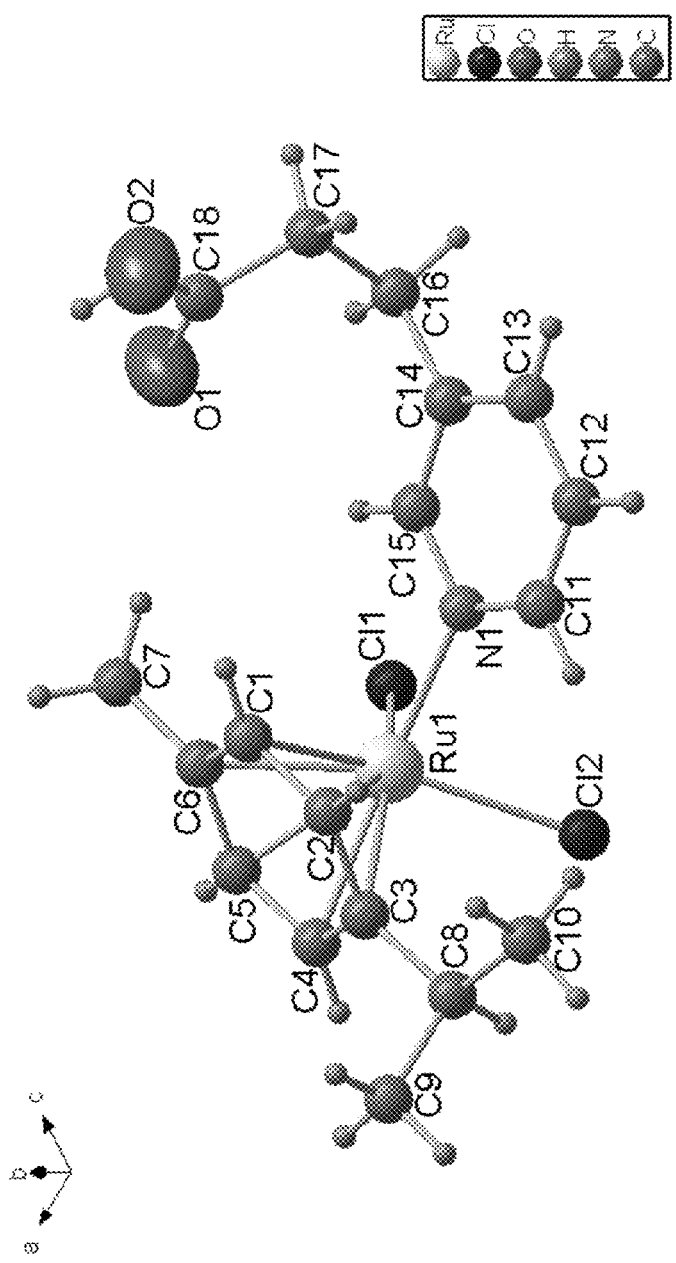
FIG. 7 presents the crystal structure of control chemical complex Ctrl-1 in accordance with various aspects and embodiments described herein.

FIG. 7 presents the crystal structure of Ctrl-1 in accordance with various aspects and embodiments described herein.

With reference back to FIG. 6, Ctrl-2 was synthesized with the same method as Ctrl-1, with DMF as the solvent in the reaction. Ctrl-2 was obtained as dark-yellow powder. Yield: 27.7 mg, 44.0%. $^1H$ NMR (400 MHz, $CDCl_3$) $\delta_{ppm}$ 9.00 (s, 1H, py), 8.95 (d, J=5.7 Hz, 1H, py), 7.65 (d, J=7.7 Hz, 1H, py), 7.26 (s, 1H, py), 5.68 (t, J=5.6 Hz, 2H, arene), 5.56 (s, 1H, arene), 5.31 (d, J=5.7 Hz, 2H, arene), 3.05-2.98 (m, 2H, $CH_2$), 2.73 (t, J=7.1 Hz, 2H, $CH_2$), 2.17 (s, 3H, $CH_3$).

Ctrl-3 was synthesized with the same method as Ctrl-2 (e.g., with DMF as the solvent in the reaction). Ctrl-3 was obtained as brown powder. Yield: 31.2 mg, 31.2%. $^1H$ NMR (300 MHz, $CDCl_3$) $\delta_{ppm}$ 8.97 (s, 1H, py), 8.95-8.90 (m, 1H, py), 7.66 (d, J=7.5 Hz, 1H, py), 5.68 (s, 6H, arene), 2.98 (s, 2H, $CH_2$), 2.73 (t, J=7.0 Hz, 2H, $CH_2$).

1.6—Synthesis of Ctrl-4

Figure 8:
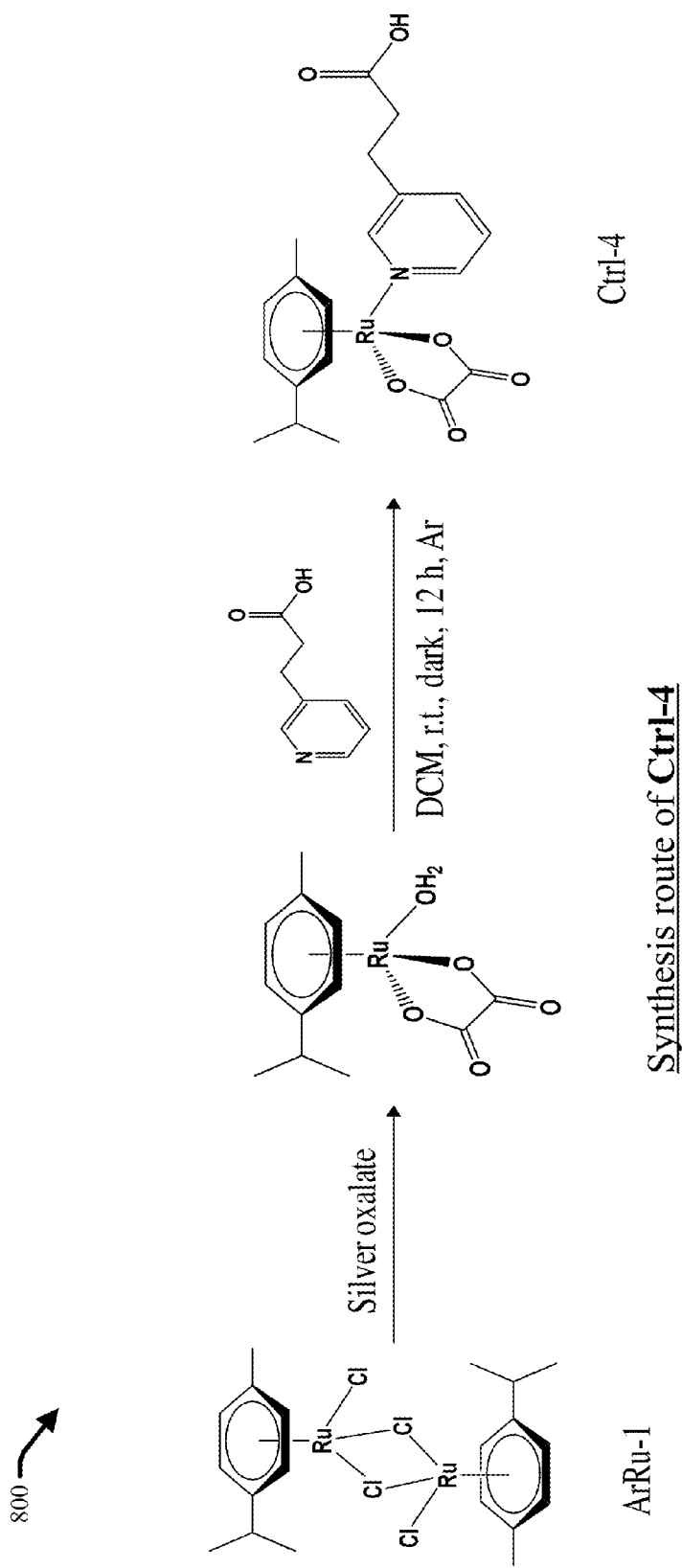
FIG. 8 presents the synthesis route of another example control chemical complex Ctrl-4 in accordance with various aspects and embodiments described herein.

FIG. 8 presents the synthesis route 800 of another example control chemical complex Ctrl-4 in accordance with various aspects and embodiments described herein.

Ctrl-4 was synthesized by the reaction of [($\eta^6$-p-cym)Ru(II)(O^O)](50.0 mg, 0.147 mmol) and 3-Pyridinepropionic acid (22.1 mg, 0.147 mmol) in DCM (10 mL) at r.t. After 4 h, an orange solution was produced and $Et_2O$ was added to get orange precipitate. Orange powder was collected by drying. Yield: 35.0 mg, 46.4%.

$^1H$ NMR (400 MHz, $CDCl_3$) $\delta_{ppm}$ 8.50 (s, 1H, py), 8.33 (d, J=5.5 Hz, 1H, py), 7.69 (d, J=7.9 Hz, 1H, py), 7.30 (d, J=5.8 Hz, 1H, py), 5.59 (d, J=6.0 Hz, 2H, arene), 5.38 (d, J=6.0 Hz, 2H, arene), 2.95 (t, J=6.9 Hz, 2H, $CH_2$), 2.87-2.60 (m, 1H, COOH), 2.84 (dd, J=13.9, 7.0 Hz, 1H, CH), 2.68 (t, J=7.0 Hz, 2H, $CH_2$), 2.10 (s, 3H, $CH_3$), 1.32 (d, J=6.9 Hz, 6H, $2CH_3$). $^{13}C$ NMR (100 MHz, DMF-$d_7$) $\delta_{ppm}$ 173.28, 165.46, 153.35, 150.52, 139.03, 138.95, 125.38, 102.20, 97.15, 82.32, 80.70, 34.84, 30.94, 28.05, 22.45, 17.86.

2—Cytotoxicity Analysis 2.1 Cell Lines and Cell Culture Conditions

Human ovarian carcinoma (A2780) and cDDP-resistant A2780 (A2780cisR) cells were cultured in RPMI 1640 with 10% FBS and 100 units penicillin/streptomycin. HeLa cells, adenocarcinomic human alveolar basal epithelial cells (A549) and cDDP-resistant A549 (A549cisR) cells were cultured in DMEM containing 10% FBS and 100 units penicillin/streptomycin. All cells were incubated at 37° C. under 5% $CO_2$. The cDDP-resistant cells, A549cisR and A2780cisR were generated from their parental A549 or A2780 cells. Briefly, A549 or A2780 cells were cultured in complete medium containing 0.5 μg/mL cisplatin at the beginning for the first screening, and the remaining cells were cultured in complete medium containing 1.0 μg/mL cisplatin for at least 4 weeks until the resistance was obtained.

2.2 Cytotoxicity Test

An MTT assay was used to evaluate the cytotoxicity of cDDP and the subject heterodinuclear Pt—Ru compounds Ruthplatin-1, 2, 3 and 4 against A2780, A2780cisR, A549, A549cisR and HeLa. The results of this assay are depicted in Table 1 of FIG. 9. Another MTT assay was used to evaluate the cytotoxicity of cDDP, Ruthplatin-1, Ctrl-1 and cDDP combined with Ctrl-1. The results of this assay are depicted in Table 2 of FIG. 10.

For each of these assays, cells were seeded in 96-well plates at a density of 1,500 cells per well (for A2780, A549 and HeLa) or 2,500 cells per well (for A2780cisR and A549cisR) and were incubated till their confluency reached about 30%. Then, medium containing different concentrations of the compounds (e.g., cDDP, Ruthplatin-1, Ruthplatin-2, Ruthplatin-3, Ctrl-1, and cDDP with Ctrl-1) was added to each well. After incubating for 72 h, the original medium was removed and 0.2 mL fresh medium containing 1 mg/mL MTT was added to each well. After staining for 4 h, the medium was replaced by DMSO. The absorbance was tested at 570 and 630 nm. A control was set as medium without compound.

FIG. 9 presents Table 1 depicting the resulting cytotoxicity of ruthplatin-1, 2, 3 and 4 as compared to the resulting cytotoxicity of cDDP. The $IC_{50}$ values represent the concentration of the tested compound required to inhibit cell growth by 50% compared to controls run in the absence of added complexes, measured by the MTT assay following a 72-h exposure. Values are the average of the 96-wells for each tested compound, and the reported errors are the corresponding standard deviations. In Table 1 the $FI^a$ (fold increase) is defined as $IC_{50}$(cDDP)/$IC_{50}$ (ruthplatin), and the $RF^b$ (resistant factor) is defined as $IC_{50}$ in A2780cisR/$IC_{50}$ in A2780, or $IC_{50}$ in A549cisR/$IC_{50}$ in A549.

As seen in Table 1 the $IC_{50}$ values for Ruthplatin-1, 2, 3 and 4 were significantly lower than that of cDDP for each of the cell lines. Compared with cisplatin, the cytotoxicity of ruthplatin-1, 2, 3 and 4 increases 7.7 to 10 times in A2780 cells, and the fold increase ranges from 37.2 to 106.7 in A2780cisR cells. The RF decreases from 17.4 for cisplatin to 3.6, 1.3, 2.7, and 2.1 for ruthplatin-1, 2, 3, and 4 respectively. Ruthplatin-1, 2, 3, and 4 also have significantly increased cytotoxicity in A549 and A549cisR cells, and the RF decreases. Ruthplatin-1, 2, 3 and 4 are also very active against the proliferation of HeLa cells.

FIG. 10 presents Table 2 depicting the resulting cytotoxicity of ruthplatin-1, Ctrl-1 and cDDP combined with Ctrl-1, as compared to the resulting cytotoxicity of cDDP. In Table 2 the $FI^a$ (fold increase) is defined as is defined as $IC_{50}$ (cDDP)/$IC_{50}$(chalcoplatin), and the $RF^b$ (resistant factor) is defined as $IC_{50}$ in A2780cisR/$IC_{50}$ in A2780, or $IC_{50}$ in A549cisR/$IC_{50}$ in A549, As seen in Table 2, ruthplatin-1 is more active than cisplatin in all the cells tested. The fold increase ranges from 4.2 to 37.2 in the different cell lines. Ruthplatin is also more active than a mixture of cDDP and Ctr-1. The RF for cDDP is 17.4 in A2780/A2780cisR cells, and it decreases to 3.6 for ruthplatin-1. Compared with that of cisplatin, the RF of ruthplatin also decreases significantly.

3—Methodologies

Figure 11:
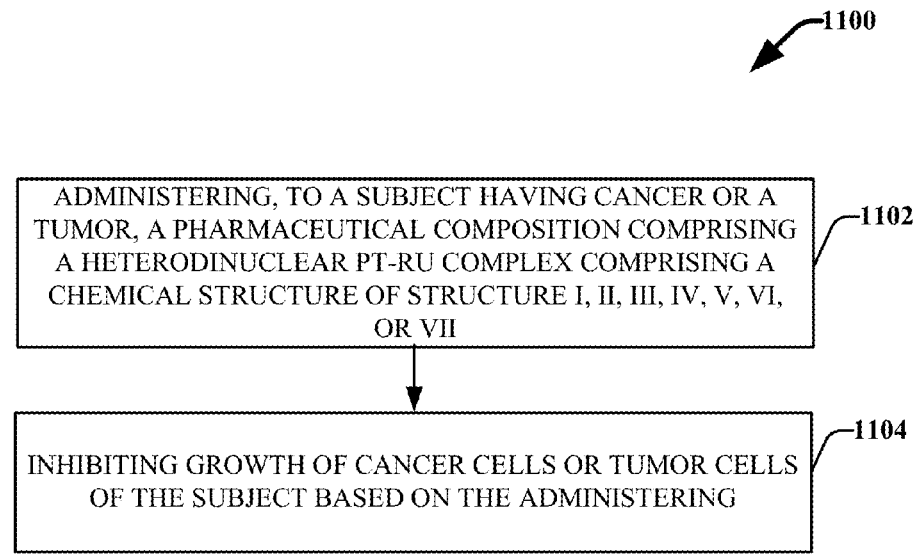
FIG. 11 provides an example method for treating a subject having cancer or a tumor in accordance with various aspects and embodiments described herein.

FIG. 11 illustrates a flow chart of an example method 1100 for treating a subject having cancer in accordance with aspects described herein. At 1102, a pharmaceutical composition comprising a heterodinuclear Pt—Ru complex with a chemical structure of Structure I, II, III, IV, V, VI, VII, VIII, IX, or X described above, is administered to a subject having cancer or a tumor. At 1104, the growth of cancer cells or tumor cells of the subject is inhibited based on the administering.

Figure 12:
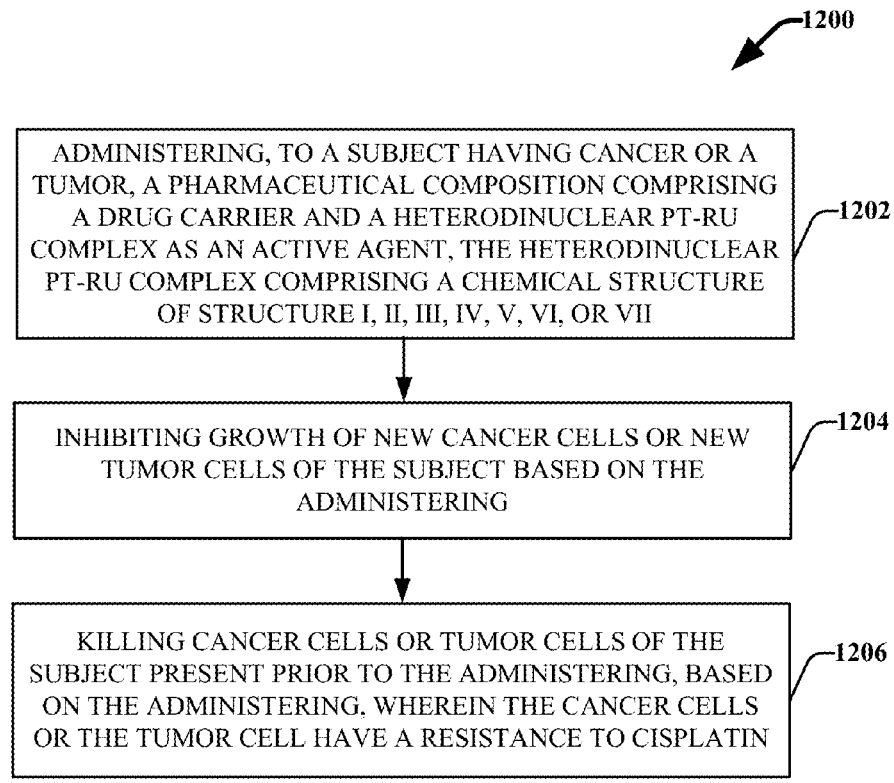
FIG. 12 provides another example method for treating a subject having cancer or a tumor in accordance with various aspects and embodiments described herein.

FIG. 12 illustrates a flow chart of an example method 1200 for treating a subject having cancer in accordance with aspects described herein. At 1202, a pharmaceutical composition comprising a drug carrier and a heterodinuclear Pt—Ru complex as an active agent is administered to a subject having cancer, wherein the chemical structure of the Pt—Ru complex corresponds to Structure I, II, III, IV, V, VI, VII, VIII, IX, or X, described above. At 1204, the growth of new cancer cells or new tumor cells of the subject is inhibited based on the administering, and at 1206, cancer cells or tumor cells of the subject present prior to the administering are killed based on the administering, wherein the cancer cells or the tumor cells have a resistance to cisplatin.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In this regard, with respect to any figure or numerical range for a given characteristic, a figure or a parameter from one range may be combined with another figure or a parameter from a different range for the same characteristic to generate a numerical range. Other than in the operating examples, or where otherwise indicated, all numbers, values and/or expressions referring to quantities of ingredients, reaction conditions, etc., used in the specification and claims are to be understood as modified in all instances by the term "about."

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of appended claims, and equivalents thereof.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A heterodinuclear platinum and ruthenium (Pt—Ru) complex having a chemical structure of Structure I:

Structure I

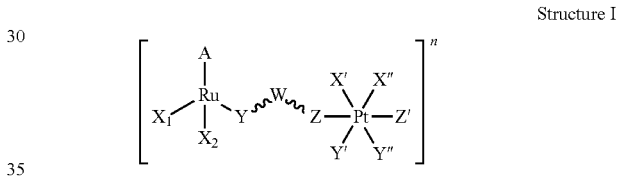

wherein $X_1$, $X_2$, X', X", Y', Y", Z, Z' are electron donor ligands selected from a group consisting of: nitrogen (N)-containing ligands, oxygen (O)-containing ligands, phosphorous (P)-containing ligands, sulfur (S)-containing ligands, and halogens, wherein Y is pyridine, wherein A is an arene, wherein W is a linker unit with any length to link Y and Z together, and wherein n is 0, any positive or negative value.

2. The heterodinuclear Pt—Ru complex of claim 1, wherein the chemical structure represents structure II:

Structure II

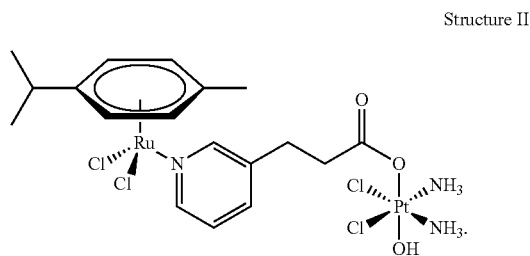

3. The heterodinuclear Pt—Ru complex of claim 2, wherein the heterodinuclear (Pt—Ru) complex is obtained via the reaction of $(\eta^6\text{-p-cym})Ru(II)Cl(\mu\text{-Cl})_2]_2$ and Pt(IV)(OH)(3-PyPA).

4. The heterodinuclear Pt—Ru complex of claim 1, wherein the chemical structure represents s structure II:

Structure II

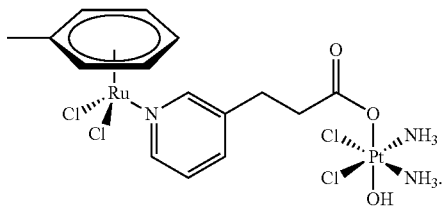

5. The heterodinuclear Pt—Ru complex of claim 4, wherein the heterodinuclear (Pt—Ru) complex is obtained via the reaction of $[(\eta^6\text{-p-cym})Ru(II)Cl(\mu\text{-Cl})_2]_2$ and Pt(IV)(OH)(3-PyPA).

6. The heterodinuclear Pt—Ru complex of claim 1, wherein the chemical structure represents structure II:

Structure II

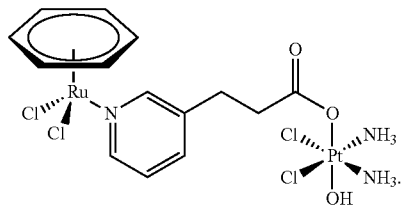

7. The heterodinuclear Pt—Ru complex of claim 6, wherein the heterodinuclear (Pt—Ru) complex is obtained via the reaction of $[(\eta^6\text{-p-cym})Ru(II)Cl(\mu\text{-Cl})_2]_2$ and Pt(IV)(OH)(3-PyPA).

8. The heterodinuclear Pt—Ru complex of claim 1, wherein the chemical structure represents structure II:

Structure II

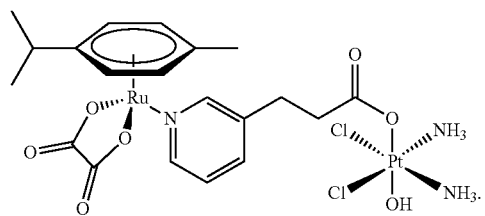

9. The heterodinuclear Pt—Ru complex of claim 8, wherein the heterodinuclear (Pt—Ru) complex is obtained via the reaction of $[(\eta^6\text{-p-cym})Ru(II)(O^\wedge O)]$ and Pt(IV)(OH)(3-PyPA).

10. A heterodinuclear platinum and ruthenium (Pt—Ru) complex having a chemical structure of Structure I:

Structure I

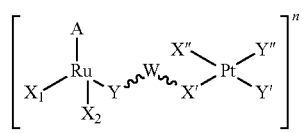

wherein $X_1$, $X_2$, X', X'', Y', Y'' are electron donor ligands selected from a group consisting of: nitrogen (N)-containing ligands, oxygen (O)-containing ligands, phosphorous (P)-containing ligands, sulfur (S)-containing ligands, and halogens, and wherein Y is pyridine,
wherein A is an arene,
wherein W is a linker unit with any length to link Y and X' together, and
wherein n is 0, any positive or negative value.

11. A method of treating cancer or a tumor in a subject, comprising:
administering, to the subject, an effective amount of a pharmaceutical composition comprising a heterodinuclear platinum and ruthenium (Pt—Ru) complex having a chemical structure of Structure I:

Structure I

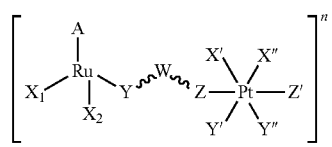

wherein $X_1$, $X_2$, X', X'', Y', Y'' Z, Z' are electron donor ligands selected from a group consisting of: nitrogen (N)-containing ligands, oxygen (O)-containing ligands, phosphorous (P)-containing ligands, sulfur (S)-containing ligands, and halogens, wherein Y is pyridine,
wherein A is an arene,
wherein W is a linker unit with any length to link Y and Z together, and
wherein n is 0, any positive or negative value.

12. The method of claim 11, further comprising:
inhibiting growth of cancer cells or tumor cells of the subject based on the administering.

13. The method of claim 12, wherein the cancer cells or the tumor cells exhibit resistance to cisplatin.

14. A method of treating cancer or a tumor in a subject, comprising:
administering, to the subject, an effective amount of a pharmaceutical composition comprising a heterodinuclear platinum and ruthenium (Pt—Ru) complex having a chemical structure of Structure I:

Structure I

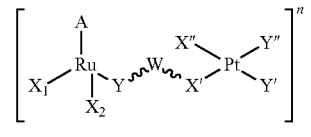

wherein $X_1$, $X_2$, X', X'', Y', Y'' are selected from electron donor ligands selected from a group consisting of: nitrogen (N)-containing ligands, oxygen (O)-containing ligands, phosphorous (P)-containing ligands, sulfur (S)-containing ligands, and halogens, and wherein Y is pyridine,
wherein A is an arene,
wherein W is a linker unit with any length to link Y and X' together, and
wherein n is 0, any positive or negative value.

15. The method of claim 14, further comprising:
inhibiting growth of cancer cells or tumor cells of the subject based on the administering.

16. The method of claim 15, wherein the cancer cells or the tumor cells exhibit resistance to cisplatin.

17. The method of claim 11, wherein the cancer or the tumor affects cells selected from a group consisting of: ovarian cells, adenocarcinoma cells, cervical cells, lung cells, breast cells, and leukemia cells.

18. The method of claim 14, wherein the cancer or the tumor affects cells selected from a group consisting of: ovarian cells, adenocarcinoma cells, cervical cells, lung cells, breast cells, and leukemia cells.

19. The method of claim 11, wherein the chemical structure of the heterodinuclear platinum and ruthenium (Pt—Ru) complex further represents structure II:

Structure II

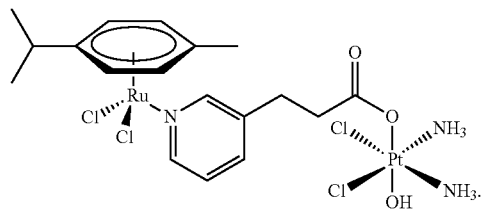

20. The method of claim 19, wherein the heterodinuclear (Pt—Ru) complex is obtained via the reaction of (η⁶-p-cym)Ru(II)Cl(μ-Cl)₂]₂ and Pt(IV)(OH)(3-PyPA).

21. The method of claim 11, wherein the chemical structure of the heterodinuclear platinum and ruthenium (Pt—Ru) complex further represents structure II:

Structure II

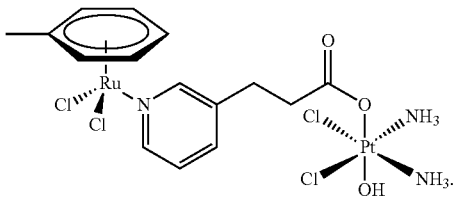

22. The method of claim 21, wherein the heterodinuclear (Pt—Ru) complex is obtained via the reaction of [(η⁶-p-cym)Ru(II)Cl(μ-Cl)₂]₂ and Pt(IV)(OH)(3-PyPA).

23. The method of claim 11, wherein the chemical structure of the heterodinuclear platinum and ruthenium (Pt—Ru) complex further represents structure II:

Structure II

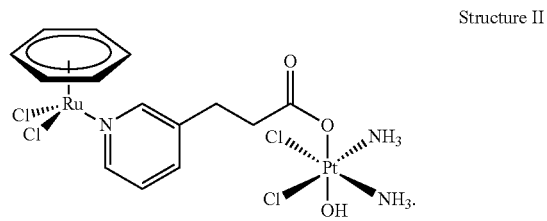

24. The method of claim 23, wherein the heterodinuclear (Pt—Ru) complex is obtained via the reaction of [(η⁶-p-cym)Ru(II)Cl(μ-Cl)₂]₂ and Pt(IV)(OH)(3-PyPA).

25. The method of claim 11, wherein the chemical structure of the heterodinuclear platinum and ruthenium (Pt—Ru) complex further represents structure II:

Structure II

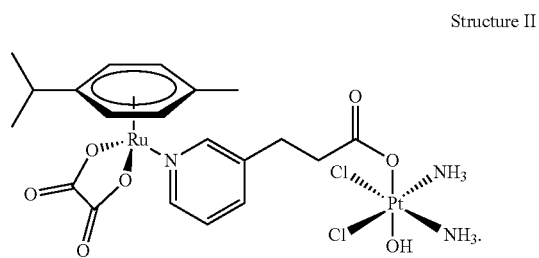

26. The method of claim 25, wherein the heterodinuclear (Pt—Ru) complex is obtained via the reaction of [(η⁶-p-cym)Ru(II)Cl(μ-Cl)₂]₂ and Pt(IV)(OH)(3-PyPA).

* * * * *